US010238703B2

(12) United States Patent
Talbott et al.

(10) Patent No.: US 10,238,703 B2
(45) Date of Patent: Mar. 26, 2019

(54) NUTRITIONAL SUPPLEMENTS AFFECTING MOOD STATE

(71) Applicants: Shawn M. Talbott, Draper, UT (US); Bryan Baranowski, Draper, UT (US)

(72) Inventors: Shawn M. Talbott, Draper, UT (US); Bryan Baranowski, Draper, UT (US)

( * ) Notice: Subject to any disclaimer, the term of this patent is extended or adjusted under 35 U.S.C. 154(b) by 0 days.

(21) Appl. No.: 15/349,851

(22) Filed: Nov. 11, 2016

(65) Prior Publication Data

US 2017/0128508 A1     May 11, 2017

Related U.S. Application Data

(60) Provisional application No. 62/254,044, filed on Nov. 11, 2015.

(51) Int. Cl.
| | |
|---|---|
| *A61K 36/00* | (2006.01) |
| *A61K 36/17* | (2006.01) |
| *A61K 36/15* | (2006.01) |
| *A61K 36/82* | (2006.01) |
| *A61K 31/522* | (2006.01) |
| *A61K 9/00* | (2006.01) |
| *A61K 31/137* | (2006.01) |
| *A61K 31/352* | (2006.01) |
| *A61K 31/455* | (2006.01) |
| *A61K 31/475* | (2006.01) |

(52) U.S. Cl.
CPC ............ *A61K 36/17* (2013.01); *A61K 9/0095* (2013.01); *A61K 31/137* (2013.01); *A61K 31/352* (2013.01); *A61K 31/455* (2013.01); *A61K 31/475* (2013.01); *A61K 31/522* (2013.01); *A61K 36/15* (2013.01); *A61K 36/82* (2013.01)

(58) Field of Classification Search
CPC .................................................... A61K 36/00
See application file for complete search history.

(56) References Cited

FOREIGN PATENT DOCUMENTS

| CN | 103860980 A | * | 6/2014 |
| CN | 103860980 A | * | 6/2014 |

OTHER PUBLICATIONS

Bang, Enzogenol improves diabetes-related metabolic change in C57BL/KsJ-db/db mice, a model of type 2 diabetes mellitus. The Journal of pharmacy and pharmacology, (Jun. 2014) vol. 66, No. 6, pp. 875-885 (Year: 2014).*

Sabu, Anti-diabetic activity of green tea polyphenols and their role in reducing oxidative stress in experimental diabetes. Journal of ethnopharmacology, (Nov. 2002) vol. 83, No. 1-2, pp. 109-116 (Year: 2002).*

Fang et al, Caffeine is responsible for the blood glucose-lowering effects of green tea and Puer tea extracts in BALB/c mice. Zhongguo Tianran Yaowu (2015), 13(8), 595-601 (Year: 2015).*

Kim et al, Hypolipidemic and antioxidant effects of quercetin in animal model of type 2 diabetes. Journal of Diabetes, (Apr. 2011) vol. 3, Supp. Suppl. 1, pp. 193 (Year: 2011).*

Ku et al, Antioxidant properties of monomeric, oligomeric, and polymeric fractions in hot water extract from Pinus radiata bark. Wood science and technology (2008), vol. 42, No. 1, pp. 47-60 (Year: 2008).*

Pullela, Isolation of lignans and biological activity studies of Ephedra viridis. Planta medica, (Aug. 2005) vol. 71, No. 8, pp. 789-791 (Year: 2005).*

* cited by examiner

*Primary Examiner* — Qiuwen Mi
(74) *Attorney, Agent, or Firm* — Holland & Hart LLP

(57) ABSTRACT

Nutritional supplement compositions for mood enhancement are disclosed. A nutritional supplement composition can include one or more of plant material from pine bark, plant material from a species of the genus *Ephedra*, caffeine, green tea, octopamine, quercetin, trimethylglycine, yohimbine, and niacin. Some nutritional supplement compositions may affect heart rate, blood pressure, and/or resting metabolic rate when ingested. Related processes are also disclosed.

22 Claims, No Drawings

NUTRITIONAL SUPPLEMENTS AFFECTING MOOD STATE

RELATED APPLICATIONS

This application claims the benefit of U.S. Provisional Application No. 62/254,044, filed on Nov. 11, 2015 and titled, "NUTRITIONAL SUPPLEMENTS AFFECTING MOOD STATE," which is hereby incorporated by reference in its entirety.

TECHNICAL FIELD

The present disclosure relates generally to the field of nutritional treatments and supplements. More particularly, the present disclosure relates to nutritional treatments and supplements for, among other things, improving one or more psychological mood states of an individual.

BACKGROUND OF THE INVENTION

Nutritional supplements are routinely used to improve health and/or physical or mental performance. While nutritional supplements may be tailored to provide specific health and/or performance benefits, relatively few supplements provide such benefits while simultaneously improving an individual's mood.

DETAILED DESCRIPTION

The present disclosure relates to nutritional treatments and supplements, and more particularly to nutritional treatments and/or supplements that improve one or more mood states of an individual. The following Detailed Description of various embodiments is not intended to limit the scope of the present disclosure, but is merely representative of various embodiments.

Amounts, concentrations, and other numerical data may be presented herein in a range format. It is to be understood that such range format is used merely for convenience and brevity and should be interpreted flexibly to include not only the numerical values explicitly recited as the limits of the range, but also all the individual numerical values or sub-ranges encompassed within that range, as if each numerical value and sub-range were explicitly recited. For example, an amount of from 1 mg to 200 mg should be interpreted to include not only the explicitly recited limits of 1 mg and 200 mg, but also individual amounts such as 2 mg, 3 mg, 4 mg, and sub-ranges such as 10 mg to 50 mg, 20 mg to 100 mg, etc. Unless otherwise stated, all ranges include both endpoints. The terms "negative mood state" and "positive mood state" are defined as described in Example 1 and elsewhere in the Detailed Description.

Nutritional supplements disclosed herein may include both (1) plant material from pine bark and (2) plant material from a species of the genus *Ephedra*. For example, in some embodiments, a nutritional supplement may include plant material from pine bark of the species *Pinus radiata* (commonly referred to as New Zealand pine). In some embodiments, the plant material is extracted from the pine bark. More particularly, in some instances, the plant material is extracted by using water as the primary (or exclusive) solvent. In some instances, the nutritional supplement includes between 10 and 100 mg; between 10 and 75 mg; between 10 and 50 mg; between 10 and 25 mg; between 25 and 100 mg; between 25 and 75 mg; between 25 and 50 mg; or between 35 and 65 mg of pine bark extract. In some embodiments, the pine bark extract, if dried, is between approximately 70-95% proanthocyanidin by weight.

In some embodiments, the species of the genus *Ephedra* from which plant material is derived may be substantially devoid of ephedrine alkaloids that have been banned by the U.S. Food and Drug Administration due to concerns about cardiovascular risk factors. More particularly, in some embodiments, the species of the genus *Ephedra* from which plant material is derived, when dried, has a total alkaloid content of less than 0.5%, 0.3%, 0.1%, and/or 0.03% by weight. In some embodiments, the species of the genus *Ephedra* from which plant material is derived is not *Ephedra sinica*, *Ephedra vulgaris*, or *Ephedra equisetina*. In some embodiments, the species of the genus *Ephedra* from which plant material is derived is *Ephedra viridis*, *Ephedra navadensis*, or *Ephedra torreyana*. In some embodiments, the nutritional supplement, including without limitation a nutritional supplement packaged for single use, includes between 15 mg and 200 mg; between 40 mg and 200 mg; between 70 mg and 200 mg; between 100 mg and 200 mg; between 150 mg and 200 mg; between 15 mg and 150 mg; between 15 mg and 100 mg; between 15 mg and 50 mg; between 40 mg and 130 mg; or between 40 mg and 75 mg of plant material from a species of the genus *Ephedra*. In some embodiments, plant material from the species of the genus *Ephedra* is between 0.1% and 0.5% of the nutritional supplement by weight.

In addition to plant material from pine bark and plant material from a species of the genus *Ephedra*, some nutritional supplements disclosed herein may include one or more of the following ingredients: green tea, green tea extract, caffeine, octopamine, quercetin, trimethylglycine (commonly referred to as betaine), yohimbine, and niacin.

For instance, in some embodiments, a nutritional supplement, including without limitation a nutritional supplement packaged for single use, includes caffeine in an amount of between 25 mg and 200 mg; between 50 mg and 200 mg; between 75 mg and 200 mg; between 125 mg and 200 mg; between 25 mg and 150 mg; between 25 mg and 125 mg; between 25 mg and 75 mg; or between 75 mg and 125 mg.

In some embodiments, a nutritional supplement (e.g., a nutritional supplement packaged for single use) may include green tea extract in an amount of between 5 mg and 75 mg. In some embodiments, the amount of green tea extract in the nutritional supplement may be between 15 mg and 65 mg.

In some embodiments, the amount of octopamine in a nutritional supplement may be between 5 mg and 150 mg. In some embodiments, the amount of trimethylglycine in a nutritional supplement may be between 15 mg and 250 mg. In some embodiments, the amount of yohimbine HCl may be between 1 mg and 20 mg. In some embodiments, the amount of niacin in a nutritional supplement may be between 1 mg and 20 mg.

In some embodiments, a nutritional supplement may be formulated as a liquid drink. For example, in some embodiments, ingredients of the nutritional supplement may be mixed into a base liquid, such as water or green tea, to form a drinkable mixture. In some embodiments, the liquid drink may be between 1 and 20 ounces in weight. In other embodiments, the nutritional supplement is formulated as one or more of a capsule, a tablet, or a powder. In some embodiments, the nutritional supplement may be packaged for single use.

In some embodiments, the nutritional supplement may be effective for increasing positive mood state, as measured by self-reported feelings of energy, mood, focus, and well-being, when the nutritional supplement is administered to a healthy adult and/or a person suffering from mood disorders. For instance, in some embodiments, the nutritional supplement may increase average positive mood state—as measured on 100 mm visual analog scales—by more than 15%, by more than 25%, by more than 40%, by more than 60%, by more than 70%, by more than 80%, and/or by more than 90%. Additionally or alternatively, as a result of consumption of the nutritional supplement, average positive mood state may increase by more than approximately 10 VAS, 15 VAS, 20 VAS, 25 VAS, and/or 30 VAS, where each VAS unit corresponds to each mm along a 100 mm visual analog scale.

Additionally or alternatively, the nutritional supplement may, in some embodiments, be effective for decreasing negative mood state, as measured by self-reported feelings of stress, tension, irritability, and anxiety, when the nutritional supplement is administered to a healthy adult and/or a person suffering from mood disorders. In some embodiments, the nutritional supplement may decrease average negative mood state—as measured on 100 mm visual analog scales—by more than 10%, by more than 15%, by more than 20%, by more than 30%, by more than 35%, and/or by more than 40%. Additionally or alternatively, average negative mood state may decrease by more than 5 VAS, 8 VAS, 10 VAS, 12 VAS, and/or 15 VAS as a result of consumption of the nutritional supplement.

In some embodiments, the nutritional supplement may exhibit thermogenic properties. Stated differently, in some embodiments, the nutritional supplement is effective for increasing resting metabolic rate when administered to a healthy adult. For example, in some embodiments, consumption of the nutritional supplement may cause an increase in resting metabolic rate of more than 1%, 2%, 3%, 4%, and/or 5%.

In some embodiments, the nutritional supplement may decrease average heart rate when administered to a healthy adult. For example, in some embodiments, the average heart rate may decrease by at least 1, 2, and/or 3 beats per minute. In some embodiments, the consumption of the nutritional supplement does not cause a change in heart rate of more than 10, more than 7, and/or more than 5 beats per minute.

In some embodiments, the nutritional supplement is effective for increasing systolic and/or diastolic blood pressure when administered to a healthy adult. For example, in some embodiments, the nutritional supplement may increase average systolic blood pressure between 4 and 20 mmHg and/or between 7 and 13 mmHg in a healthy adult. In some embodiments, the nutritional supplement may increase average diastolic blood pressure between 4 and 13 mmHg and/or between 6 and 12 mmHg when administered to a healthy adult. In some embodiments, administration of the nutritional supplement does not cause a change in systolic or diastolic blood pressure of more than 18 mmHg, 15 mmHg, and/or 12 mmHg. Thus, the nutritional supplement may provide one or more health benefits, while blood pressure and heart rate remain within healthy ranges.

Example 1

Experimental Design

A study was conducted to evaluate the effect of using a nutritional supplement drink that includes both plant material from *Ephedra viridis* and plant material from New Zealand pine (*Pinus radiata*) bark. More particularly, a 4-ounce nutritional supplement drink was made that included the ingredients set forth in Table 1 in a green tea. The amount of each listed ingredient in the 4-ounce drink is also set forth in the same table.

TABLE 1

| Ingredient | Amount in a single serving |
| --- | --- |
| Powdered *Ephedra viridis* | 62.5 mg |
| Extract from New Zealand pine (*Pinus radiata*) bark (Enzogenol ®) | 50 mg |
| Green tea extract (approximately 60% epigallocatechin gallate) | 25 mg |
| Caffeine (anhydrous) | 100 mg |
| Octopamine | 25 mg |
| Quercetin | 25 mg |
| Trimethylglycine (anhydrous) | 62.5 mg |
| Yohimbine HCl | 3.75 mg |
| Niacin | 3.75 mg |

Eight healthy active adult subjects (3 male, 5 female; average age=45±9; average BMI=22.8) were recruited to participate in three two-hour interventions. In the first intervention (i.e., the control intervention), none of the eight subjects was given a nutritional supplement drink. In the second intervention, each of the eight subjects was given a single serving (4 ounces) of a nutritional supplement drink that includes the ingredients and amounts listed in Table 1. In the third intervention, each subject was given an 8-ounce nutritional supplement drink in which the amount of each of the ingredients set forth in Table 1, with the exception of New Zealand pine bark extract, was doubled. In the third intervention, the amount of New Zealand pine bark extract remained constant at 50 mg. The study was conducted over a seven-day period, with each intervention spaced three days apart.

Each subject's systolic blood pressure, diastolic blood pressure, and heart rate were measured at baseline (i.e., immediately before consumption of the nutritional supplement drink for the single-serving and double-serving interventions and at t=0 h for the control intervention) and at each 15-minute interval thereafter for two hours. Each subject's resting metabolic rate was measured at baseline (i.e., t=0 h) and at two hours thereafter.

During each intervention, the mood state of each subject was analyzed at baseline and at each 15-minute interval thereafter through the use of 100 mm visual analog scales. More specifically, negative mood state was assessed by asking each participant to mark 100 mm visual analog scales in a manner that reflects their subjective perception of mood state parameters relating to negative mood state (i.e., stress, tension, irritability, anxiety) and positive mood state (i.e., energy, mood, focus, well-being). A mark on the far left side of the visual analog scale (corresponding to 0 VAS) meant that the specified parameter was not noticeable, while a mark on the far right side of the scale (corresponding to 100 VAS) meant that the subject perceived the maximal amount with respect to that parameter. The scores from the four mood state parameters for negative mood state were averaged to determine the negative mood state at each time point. Scoring for the positive mood state was calculated in an analogous manner.

Results

The average systolic blood pressure of subjects after consumption of the single-serving nutritional supplement (120±2 mmHg) and the double-serving nutritional supplement (121±4 mmHg), as measured by averaging the eight time points after consumption, was significantly increased (p<0.05) by approximately 10% compared to the control intervention (109±2 mmHg). Similarly, the diastolic blood pressure of subjects after consumption of the single-serving (81±3 mmHg) and double-serving (83±3 mmHg) nutritional supplement was increased compared to the control intervention (73±2 mmHg).

The average post-consumption heart rate in the single-serving and double-serving interventions (64±5 bpm) was about 5% lower than the average heart rate in the control intervention (61±2 bpm). Further, the average post-consumption resting metabolic rate for the single-serving (1502±30 kcal) and the double-serving (1527±123 kcal) interventions was elevated compared to the average resting metabolic rate for the control intervention (1456±32 kcal).

Additionally, the subjects reported an overall improvement of mood state in the single-serving and double-serving interventions relative to the control intervention. More particularly, the average post-consumption negative mood state for the single-serving (26±4 VAS) and double-serving (27±5 VAS) interventions was decreased relative to the average negative mood state reported by subjects for the control intervention (44±9 VAS). Conversely, the average post-consumption positive mood state for the single-serving (70±4 VAS) and double-serving (60±9 VAS) interventions was significantly increased (p<0.05) relative to the average positive mood state (35±7 VAS) reported by subjects for the control intervention. Without being limited to any particular theory, it is believed that the combination of both increased positive mood state and decreased negative mood state that is elicited by the nutritional supplement of Example 1 is a characteristic that is markedly different from any of the individual components of the nutritional supplement in their natural state.

In short, single and double servings of the nutritional supplement described in this example increased average blood pressure and reduced heart rate within normal healthy ranges. Both nutritional supplements also elevated resting metabolic rate. Further, and unexpectedly, the nutritional supplement produced both a decrease in negative mood state and an increase in positive mood state.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

This disclosure should not be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

It will be apparent to those having skill in the art that changes may be made to the details of the above-described embodiments without departing from the underlying principles of the present disclosure.

The invention claimed is:

1. A nutritional supplement comprising:
between 10 mg and 100 mg pine bark extract; and
between 15 mg and 200 mg plant material from a species of the genus *Ephedra*; wherein the nutritional supplement is effective for increasing positive mood state.

2. The nutritional supplement of claim 1, wherein the pine bark extract is from the species *Pinus radiata*.

3. The nutritional supplement of claim 1, wherein the plant material from a species of the genus *Ephedra* when dried, has a total alkaloid content of less than 0.1% by weight.

4. The nutritional supplement of claim 1, wherein the plant material from a species of the genus *Ephedra* is not from *Ephedra sinica*, *Ephedra vulgaris*, or *Ephedra equisetina*.

5. The nutritional supplement of claim 1, wherein the plant material from a species of the genus *Ephedra* is from *Ephedra viridis*, *Ephedra nevadensis*, or *Ephedra torreyana*.

6. The nutritional supplement of claim 5, wherein the plant material from a species of the genus *Ephedra* is from *Ephedra viridis*.

7. The nutritional supplement of claim 1, wherein the nutritional supplement comprises between 40 mg and 130 mg of plant material from a species of the genus *Ephedra*.

8. The nutritional supplement of claim 1, further comprising one or more of green tea extract and caffeine.

9. The nutritional supplement of claim 1, further comprising green tea extract and caffeine.

10. The nutritional supplement of claim 8, wherein the nutritional supplement comprises between 25 mg and 200 mg of caffeine.

11. The nutritional supplement of claim 8, wherein the nutritional supplement comprises between 5 mg and 75 mg of green tea extract.

12. The nutritional supplement of claim 1, wherein the nutritional supplement is formulated as a liquid drink.

13. The nutritional supplement of claim 12, wherein the liquid drink is between 1 and 20 ounces in weight.

14. The nutritional supplement of claim 1, wherein the plant material from the species of the genus *Ephedra* is between 0.1% and 0.5% of the nutritional supplement by weight.

15. The nutritional supplement of claim 1, further comprising one or more of: octopamine; quercetin; trimethylglycine; yohimbine; and niacin.

16. The nutritional supplement of claim 1, further comprising: octopamine; quercetin; trimethylglycine; yohimbine; and niacin.

17. The nutritional supplement of claim 1, wherein the nutritional supplement is effective for increasing positive mood state when administered to a healthy adult.

18. The nutritional supplement of claim 1, wherein the nutritional supplement is effective for decreasing negative mood state when administered to a healthy adult.

19. The nutritional supplement of claim 1, wherein the nutritional supplement is effective for increasing resting metabolic rate when administered to a healthy adult.

20. The nutritional supplement of claim 1, wherein administration of the nutritional supplement to a healthy adult does not cause: a change in systolic or diastolic blood pressure of more than 18 mmHg; or a change in heart rate of more than 10 beats per minute.

21. The nutritional supplement of claim 1, wherein the nutritional supplement is packaged for single use.

22. A method of altering the mood state of a subject, the method comprising:
   obtaining the nutritional supplement of claim 1; and
   ingesting the nutritional supplement.

* * * * *